United States Patent
Santhanam et al.

(10) Patent No.: US 6,277,881 B1
(45) Date of Patent: Aug. 21, 2001

(54) TURMERIC AS AN ANTI-IRRITANT IN COMPOSITIONS CONTAINING HYDROXY ACIDS OR RETINOIDS

(75) Inventors: Uma Santhanam, Tenafly; Ronni Lynn Weinkauf, River Edge; Laura Rose Palanker, Jackson, all of NJ (US)

(73) Assignee: Unilever Home & Personal Care, USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/542,302

(22) Filed: Apr. 4, 2000

Related U.S. Application Data

(60) Provisional application No. 60/136,191, filed on May 27, 1999.

(51) Int. Cl.⁷ .................................................. A01N 37/00
(52) U.S. Cl. ..................... 514/529; 514/558; 514/560; 514/578; 514/675
(58) Field of Search ......................... 514/558, 578, 514/500, 529, 675

(56) References Cited

U.S. PATENT DOCUMENTS 5,053,222 * 10/1991 Takasu et al. ........................ 424/7
5,152,983 * 10/1992 Nambudiry et al. ................. 424/60
5,861,415 * 1/1999 Majeed et al. ....................... 514/321
5,925,376 * 7/1999 Heng ..................................... 424/451
6,190,678 * 2/2001 Hasenoehrl et al. ................. 424/401

OTHER PUBLICATIONS

Huang et al. "Inhibitory Effects of Curcumin on Tumorigenesis in Mice", Journal of Cellular Biochemistry Supplement 27:26–34 (1997).
Mukundan et al. "Effect of turmeric and curcumin on BP–DNA adducts", Carciogenesis, vol. 14, No. 3, pp. 493–496 (1993).
Huang et al. "Inhibitory Effects of Curcumin on in Vitro Lipoxygenase and Cyclooxygenase Activities in Mouse Epidermis", Cancer Research 51, 813–819 (1991).
Kuttan et al, Tumori, vol. 28, #73(1), pp29–31 (abstract), Feb. 1987.*
Conney et al, Proc. Soc. Exp. Biol. Med., vol. 216 #2, pp. 234–245 (abstract), Nov. 1997.*
Huang et al, Cancer Res., vol. 51, #3, pp. 813–819 (abstract), Feb. 1991.*
Lu et al, Carcinogenisis, vol. 15, #10, pp. 2363–2370 (abstract), Oct. 1994.*

* cited by examiner

*Primary Examiner*—James H Reamer
(74) *Attorney, Agent, or Firm*—Milton Honig

(57) ABSTRACT

Compositions containing hydroxy acids and/or retinoids and further containing turmeric extract as an anti-irritant/anti-sting agent.

6 Claims, No Drawings

TURMERIC AS AN ANTI-IRRITANT IN COMPOSITIONS CONTAINING HYDROXY ACIDS OR RETINOIDS

This applications claims the benefit of Provisional No. 60/136,191 filed May 27, 1999.

FIELD OF THE INVENTION

The present invention relates to the use of turmeric in a composition and a method for reducing or eliminating skin irritation or sting induced by hydroxy acids or retinoids.

BACKGROUND OF THE INVENTION

Hydroxy acids (HAs) and retinoids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g., skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy due to a decreased HA penetration through the skin. It is desirable to reduce or eliminate the irritation potential of HAs and/or retinoids while maintaining their efficacy.

Turmeric is a powdered rhizome of the plant *Curcuma longa* Linn. The biological activities of turmeric have generally been attributed to curcumin, a component of turmeric extract. Curcumin has been reported to have anti-inflammatory and anti-oxidant activity. See Huang et al., "Inhibitory Effects of Curcumin on Tumorigenesis in Mice", Journal of Cellular Biochemistry Supplement 27:26–34 (1997), Mukundan et al., "Effect of turmeric and curcumin on BP-DNA adducts", Carciogenesis, Vol. 14, No. 3, pp. 493–496 (1993) and Huang et al., "Inhibitory Effects of Curcumin on in Vitro Lipoxygenase and Cyclooxygenase Activities in Mouse Epidermis", Cancer Research 51, 813–819 (1991).

U.S. Pat. No. 5,053,222 (Takasu et al.) discloses a hair cosmetic composition for dandruff treatment which may contain a variety of optional ingredients, including certain alpha-hydroxy acids, vitamin A, and turmeric. U.S. Pat. No. 5,152,983 (Nambudiry et al.) discloses sunscreen compositions comprising a 1,3-diketone, which may be curcumin. The 1,3-diketone is present in the Nambudiry composition at 0.01 to 15%. By contrast, the curcumin content in the compositions of the present invention, even if up to 20% of turmeric extract is used, is at most 0.0002%, i.e., orders of magnitude below the minimum amount in the Nambudiry patent. If turmeric extract were used at levels sufficient to provide curcumin amount of Nambudiry patent, unacceptable yellow color would result.

The art discussed above does not teach any compositions containing turmeric extract at a level presently claimed in combination with HAs and/or retinoids. The art does not appear to teach the use of turmeric extract or curcumin to reduce irritation or sting associated with the use of HAs and/or retinoids. Even more importantly, the art does not disclose the criticality of employing turmeric extract rather than curcumin, to reduce skin irritation. On the contrary, the literature appears to equate the activities of turmeric extract and curcumin.

SUMMARY OF THE INVENTION

The present invention includes, in part, a composition containing a cosmetic benefit ingredient selected from the group consisting of hydroxy acids ("HAs") and certain retinoids and further containing turmeric extract.

The invention also includes a method for reducing irritation or sting induced by the topical application of a composition containing HAs or retinoids, the method comprising topically applying turmeric extract. According to the inventive method, turmeric extract may be co-present with HAs and/or retinoids in the same composition, or turmeric extract may be applied from a separate composition.

According to the present invention, by virtue of topical application of turmeric extract, the irritation or sting induced by the topical application of HAs and/or retinoids is reduced or eliminated. It has been found as part of the present invention that not all known anti-irritants, ameliorate HA/retinoid induced irritation.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition unless otherwise specified.

Turmeric extract is an essential ingredient of the inventive compositions and is employed according to the present invention to reduce or eliminate the skin irritation induced by hydroxy acids and/or retinoids.

The amount of turmeric extract in the inventive compositions ranges generally from 0.01 to 20% by weight of the composition, preferably from 0.1% to 10%, most preferably from 1% to 5%.

Hydroxyacids enhance proliferation and increase ceramide biosynthesis in keratinocytes, increase epidermal thickness, and increase desquamation of normal skin resulting in smoother, younger looking skin.

The hydroxy acid can be chosen from alpha-hydroxy acids, beta-hydroxyacids (e.g., salicylic acid), other hydroxycarboxylic acids (e.g., dihydroxycarboxylic acid, hydroxy-dicarboxylic, hydroxytricarboxylic) and mixtures thereof or combination of their stereoisomers (DL, D or L).

Preferably the hydroxy acid is chosen from alpha-hydroxy acids having the general structure (1):

(1)

where M is hydrogen or a saturated or an unsaturated, straight or branched hydrocarbon chain containing from 1 to 27 carbon atoms.

Even more preferably the hydroxy acid is chosen from lactic acid, 2-hydroxyoctanoic acid, hydroxylauric acid, glycolic acid, and mixtures thereof. When stereo isomers exist, L-isomer is most preferred.

It is to be understood that depending on the pH of the composition, the hydroxy acid may be present as a salt, e.g., ammonium or potassium or sodium salt.

Although the inventive compositions may have any pH in the general range of 2.0 to 10, the inventive compositions are particularly useful when they are at an acidic pH (especially if they contain a hydroxy acid), most preferably at a pH of 2 to 4, because such compositions are particularly irritating.

Retinoids enhance keratinocyte proliferation in vitro, increase epidermal thickness and increase collagen synthesis by dermal fibroblasts. This results in protection from sun damage and smoothing of wrinkled skin. The term "retinoids" as used herein includes retinoic acid, retinol, retinal and $C_2$–$C_5$ retinyl esters, because these are the most irritating. Included in the term "retinoic acid" are 13-cis retinoic acid and all-trans retinoic acid.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_2$–$C_5$ esters of retinol, preferably $C_2$ and $C_3$ esters, and most preferably $C_2$ ester because it is more commonly available. Retinyl esters included in the invention are also known as: retinyl acetate, retinyl propionate, retinyl butyrate, and retinyl pentanolate.

A particular advantage of the inventive compositions is that higher amounts of hydroxy acids or retinoids may be employed without causing skin irritation. Preferably the amount of the hydroxy acid component present in the composition according to the invention is from 0.01 to 20%, more preferably from 0.1 to 12% and most preferably from 4 to 12% by weight.

A retinoid may be present in the inventive compositions in an amount 33 to 330,000 IU per gram of the composition, preferably 330 to 16,500 IU, most preferably 1,650 to 6,600 IU. Again, a higher amount of a retinoid may be employed in the inventive compositions without causing skin irritation, due to the co-presence of Turmeric extract.

Most preferred inventive compositions containing turmeric extract anti-irritant include retinol and/or retinyl acetate and/or glycolic acid and/or lactic acid because these ingredients have been found to cause irritation yet they were found to be particularly efficacious at delivering cosmetic benefits.

The skin treatment composition of the invention also includes a cosmetically acceptable vehicle or a carrier which is inert, usually an ingredient present in the highest amounts, and functioning to deliver active or performance ingredients.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

According to the present invention, the vehicle is preferably at least 60 wt % water, by weight of the vehicle. The inventive compositions are preferably oil-water emulsions, in order to improve dermal delivery of hydroxy acids (See Sah A., "An in-vitro study of the effect of formulation variables and product structure on the delivery of alpha-hydroxy acid (Lactic acid) to skin", MS Thesis, Department of Pharmaceutical Sciences of the College of Pharmacy, University of Cincinnati, Ohio, July 1996). Such improved delivery is frequently accompanied by increased irritation/sting, making the use turmeric extract in such emulsions particularly critical. In the preferred oil-in-water emulsions according to the present invention, water comprises at least 50 wt % of the inventive emulsion, most preferably from 50 to 70 wt %, by weight of the composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other component materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

According to the present inventive method, the skin irritation induced by the active ingredient is reduced or eliminated by topical application of turmeric extract. The turmeric extract may be co-present with the active, or it may be applied to the skin separately from the active.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The turmeric extract may be packaged separately from the composition containing HAs and/or retinoids.

The following specific examples further illustrate the invention, but the invention is not limited thereto. Turmeric extract employed in the examples was obtained from C.V. Alam Sari, Indonesia, under the tradename Extract Curcuma/Extract Temugiring. It contained 0.0009% curcumin.

EXAMPLE 1

This example investigated the anti-irritant capability of turmeric and curcumin using an in vitro test. It is known that the cytokine interleukin-1 (IL-1) has pro-inflammatory effects in the skin. IL-1 causes release of prostaglandin E2 (PGE2) which, in turn, can be responsible for irritation in the skin. A compound that can inhibit the PGE2 release caused by IL-1 can be expected to have anti-irritant properties. Furthermore, it has been reported that agents such as hydroxy acids can cause the release of IL-1 in skin. This example examined the ability of test compounds to inhibit the induction of PGE2 by the cytokine IL-1.

Neonatal human dermal fibroblasts (obtained from Clonetics Corp., San Diego, Calif.; passage 5–9) were seeded at a density of 7500 cells per well in 96-well tissue culture treated plates (Corning-Costar, Corning, N.Y.). The medium used was Dulbecco's Modified Eagle's Medium (DMEM), high-glucose (Life Technologies, Gaithersburg, Md.) supplemented with 2 mM L-glutamine, 10% fetal bovine serum, and antibiotic and anti mycotic solutions (all also Life Technologies). After 48 hours, each well was rinsed twice with 200 µl serum-free DMEM and the cells dosed with 200 µl in DMEM+L-glutamine containing IL-1 at 1 ng/ml or IL-1 plus test compound (turmeric extract or curcumin). Curcumin was purchased from Sigma. After six hours, cells were examined microscopically for qualitative viability, and the medium was harvested and frozen until analysis. Each treatment was run in quadruplicate.

Enzyme immunoassay was performed using a commercial PGE2 kit (Amersham, Buckinghamshire, England). PGE2-specific antibody is precoated on a set of microtiter wells. The assay is based on the competition between unlabelled PGE2 (standard or sample) and a fixed quantity of peroxidase labeled PGE2 for a limited amount of the well-bound PGE2-specific antibody. Standards of 0, 1, 2, 4, 8, 16, and 32 pg/well or 50 µl media/well were applied with 50 µl/well of 0.1 M phosphate buffer pH 7.5 for 3 hours at 4° C. At the end of this incubation, 50 µl/well of horseradish peroxidase-conjugated PGE2 was added to all wells and the plate incubated for 1 hour at 4° C. Plates were washed 4 times with 300 µl/well 0.01 M phosphate buffer pH 7.5 containing 0.5% Tween 20. 150 µl/well 3,3',5,5'-tetramethylbenzidine/hydrogen peroxide substrate in 20% dimethylformamide was added and the plate incubated exactly 30 minutes at room temperature. Reaction was stopped by adding 100 µl/well 1 M sulfuric acid. The Spectramax 340 microplate spectrophotometer (Molecular Devises, Sunnyvale, CT) was used to quantitate color in the wells by reading absorbance at 450 nm. A standard curve was plotted and the amount of PGE2 in the samples was extrapolated from the curve.

The anti-irritant potential of the test compounds is assessed by the ability of the compound to inhibit IL-1-induced PGE2. The higher percent inhibition, the more effective the anti-irritant. Statistical significance was determined using the student's t-test. The results that were obtained are summarized in Table 1.

TABLE 1

| TREATMENT | PG/ML (AVG, N = 4) | % INHIBITION OF IL-1-INDUCED PGE2 | P VS IL-1 |
|---|---|---|---|
| Expt. 1 control | 26.5 | | |
| IL-1 | 480.9 | | |
| IL-1 + turmeric 0.005% | 22.7* | 100 | <0.001 |
| IL-1 + turmeric 0.001% | 14.1* | 102 | <0.001 |
| Expt. 2 control | 165.3 | | |
| IL-1 | 768.6 | | |
| IL-1 + turmeric 0.01% | 123.1 | 107 | 0.88 |
| IL-1 + turmeric 0.002% | 63.6* | 116 | 0.005 |
| Expt. 3 control | 945.8 | | |
| IL-1 | 5545.7 | | |
| IL-1 + curcumin 0.01% | 745.7* | 104 | 0.018 |
| IL-1 + curcumin 0.002% | 458.5* | 110 | 0.005 |
| Expt. 4 control | 149.0 | | |
| IL-1 | 279.7 | | |
| IL-1 + curcumin 0.01% | 396.7 | ** | 0.2 |
| IL-1 + curcumin 0.001% | 206.5 | 56 | 0.39 |

*Significantly different from IL-la, $p < 0.05$, student's t-test
**Increase in PGE 2 (increase in irritation)

The results in Table 1 demonstrate that both curcumin and turmeric extract exhibit anti-irritant activity in this test but the following analysis shows that the activity of the turmeric extract is not due to curcumin: The turmeric extract used in the above experiments was a 0.36% ethanolic extract of turmeric. It has been reported that curcumin content of harvested turmeric is 0.1% to 0.24% (Curcumin content of cultivated turmeric in Korea, Chi et al. Saengyak Hakhoechi (1983) 14 (2) 67–69). Assuming a curcumin content of 0.25%, the concentration of curcumin in the turmeric extract used here was 0.0009%. When used at 0.001% in the test (expt. 1), this would have contained only $0.9 \times 10^{-6}$% curcumin. Expt. 3 indicates that a concentration of 0.002% curcumin is required to give an activity comparable to 0.001% turmeric, therefore, it is evident that the activity of turmeric is not due to its curcumin content.

EXAMPLE 2

Subjects were tested according to Irritation Test Method described below.

Irritation Test Method

Four Exposure Patch Test: The objective was to compare the level of irritation produced by various test materials after repeated patch applications. The test materials were held in contact with the skin under occlusive conditions. The outer upper arm of the panelist was designated as the area of application. Bandage type dressing (Scanpor® tape) was used to hold the patches (25 mm Hill Top® Chamber fitted with 18 mm diameter disc of Webril® padding) into place.

Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday and Friday of the study, prior to re-patching.

Skin irritation such as moderate redness, dryness, and/or itching of the test site is expected. Swelling of the test sites is possible. If any test has moderate redness or any swelling at evaluation, that particular test site should not be repatched.

The test sites on each arm were visually ranked by two trained examiners under consistent lighting. The test sites were ranked in order of severity. The examiner ranking responses at the first evaluation period continued ranking the sites each day throughout the study.

In ranking the reactions, the site with the most severe response was given the lowest score. The site with the second most severe response was given the second lowest score, etc. There was no forced ranking. If two or more sites had no response or the same response (no difference between sites), an average of the ranks was assigned. If a site has been discontinued, due to degree of irritation the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid and/or retinoid, using Friedman's Rank Sum. Treatments were compared to the Formula 2 at each evaluation point using Friedman's analysis with the panelist acting as a block (i.e., each panelist was tested with each test treatment). p-value of <0.1 was considered statistically significant.

EMULSION BASE FORMULA

| FULL CHEMICAL NAME OR CFTA NAME | TRADE NAME AND % ACTIVE AS RECEIVED | WT. % |
|---|---|---|
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam, Emulsion | 0.01 |
| butylene glycol 1,3 | Butylene Glycol 1,3 | 3.0 |
| hydroxyethylcellulose | Natrosol 250HHR | 0.5 |
| glycerine, USP | Glycerine USP | 2.0 |
| xanthan gum | Keltrol 1000 | 0.2 |
| triethanolamine | Triethanolamine 99 (%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12-15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| sodium stearoyl lactylate | Pationic SSL | 0.5 |
| retinyl palmitate | Vit. A Palmitate 84% | 0.06 |
| hydroxy caprylic acid | Hydroxy caprylic acid | 0.1 |
| water, DI | | q.s. to 99.80 |
| alpha-bisabolol | Alpha-bisabolol | 0.2 |
| pH | | 7–8 |

Additional ingredients in the Examples below were added in place of water.

Compositions containing ingredients as indicated in Tables 2 and 2A were tested using the Irritation Test Method. Twenty subjects were tested for Table 2 test and 17 for Table 2A test. The results that were obtained are summarized in Tables 2 and 2A. The higher the Sum of Ranks, the less severe the irritation.

TABLE 2

Irritation Test Results

| COMPOSITION | INGREDIENTS | SUM OF RANKS (DAY 4) |
|---|---|---|
| 1 | Base Formula | 68.5[a] |
| 2 | Control: Base Formula + 8% Glycolic Acid and 0.075% Retinol | 46.5 |
| 3 | Composition #2 + 3% Black Currant Seed Oil | 58.0 |
| 4 | Composition #2 + 1% Sambucus | 44.5 |

*Significantly less irritating than composition #2.

TABLE 2A

Irritation Test Results

| COMPOSITION | INGREDIENTS | SUM OF RANKS (Day 4) |
|---|---|---|
| 1 | Base Formula | 77.5 |
| 5 | Base Formula + 8% Glycolic acid | 61.0 |
| 6 | Base Formula + 8% Glycolic acid + 2.5% Ethanol[a] | 56.5 |
| 7 | Composition #5 + 2.5% turmeric extract | 80.0[b] |

[a]Ethanol was tested as turmeric extract was in ethanol.
[b]Significantly less irritating than compositions 5 and 6.

It can be seen from the results in Table 2 that after four exposures, 8% glycolic acid with 0.075% retinol (composition #2) was significantly more irritating than Base formula #1. 1% Sambucus (#4) or 3% Black Currant Seed Oil (#3) did not significantly reduce the irritation. Sambucus and Black currant seed oil are known anti-irritants. However, neither agent was effective in reducing alpha hydroxy acid/retinol induced irritation.

By contrast, as demonstrated by the results in Table 2A, turmeric extract (composition #7) significantly reduced the irritation induced by Composition 5 (containing 8% glycolic acid) and composition 6 (containing 8% glycolic and ethanol—the more appropriate control for this experiment).

COMPARATIVE EXAMPLE 3

Compositions 1, 2 and 11–14 containing ingredients as indicated in Table 3 were tested using the Irritation Test Method described in Example 2. Seventeen subjects were tested. The results that were obtained are summarized in Table 3. The higher the sum of ranks, the less is the irritation.

TABLE 3

Irritation Test Results

| COMPOSI-TION # | INGREDIENTS | SUM OF RANKS (DAY 4) |
|---|---|---|
| 1 | Base Formula | 74.5[a] |
| 2 | Base Formula + 8% Glycolic + 0.075% Retinol | 61.5 |
| 11 | Composition #2 + 1% Green Tea | 51.0 |
| 12 | Composition #2 + 0.1% K2 Glycyrrohetinic Acid | 54.5 |
| 13 | Composition #2 + 3% Quench T* | 58.5 |
| 14 | Composition #2 + 3% Polyol Prepolymer-2** | 57.0 |

[a]Statistically less irritating than composition #2.
*An anti-irritant from Centerchem (containing water, butylene glycol, kola bean extract, guarana extract, and mate extract).
**An anti-irritant from Penederm, Inc. (CFTA name PPG-12/SMDI).

It can be seen from the results in Table 3 that none of the known anti-irritants tested were able to significantly reduce the irritation induced by composition #2 (containing 8% Glycolic Acid and 0.075% Retinol).

EXAMPLE 4

A typical oil-in-water emulsion within the scope of the invention is as follows:

| chemical name | wt % |
|---|---|
| propylene glycol | 1.0 |
| glycerin | 1.0 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2.0 |
| isopropyl palmitate | 5.0 |
| dimethicone | 0.5 |
| cholesterol | 0.5 |
| cetyl alcohol | 0.5 |
| isostearic acid | 3.0 |
| retinyl palmitate | 0.1 |
| peg-40 stearate | 1.0 |
| peg-100 stearate | 1.0 |
| sorbitan stearate | 1.0 |
| turmeric extract | 0.5 |
| glycolic acid | 7.0 |
| ammonium hydroxide | to pH 4.0 |
| water DI | qs to 100% |

EXAMPLE 5

Another typical oil-in-water emulsion within the scope of the invention is as follows:

| chemical name | wt % |
|---|---|
| propylene glycol | 1.0 |
| hydroxyethylcellulose | 0.5 |
| magnesium aluminum silicate | 0.5 |
| imidazolidinyl urea | 0.2 |
| petrolatum | 2.0 |
| isopropyl palmitate | 5.0 |
| dimethicone | 0.5 |
| cholesterol | 0.5 |
| stearic acid | 3.0 |
| isostearic acid | 1.5 |
| glycerol stearate | 1.5 |
| peg-40 stearate | 1.0 |
| peg-100 stearate | 1.0 |
| sorbitan stearate | 1.0 |
| cetyl alcohol | 0.5 |
| turmeric extract | 2.0 |
| glycolic acid | 10.0 |
| ammonium hydroxide | to pH 3.8 |
| water DI | qs to 100% |

EXAMPLE 6

A typical water-in-oil dispersion within the scope of the invention is as follows:

| chemical name | wt % |
|---|---|
| isostearyl neopentanoate | 20.0 |
| peg-8 caprylic/capric glycerides | 6.0 |
| cetyl octanoate | 17.0 |
| polyglyceryl-6 dioleate | 15.0 |
| cyclomethicone | 20.0 |
| glyceryl isostearate | 0.5 |
| isostearic acid | 0.5 |
| ceramide III | 0.1 |
| ppg-5-cetheth-20 | 3.0 |
| L-lactic acid/potassium lactate | 6.0 |
| hydroxycaprylic acid | 0.1 |
| water DI | 1.3 |
| turmeric extract | 0.5 |

EXAMPLE 7

The following oil-in-water emulsion within the scope of the invention is prepared:

| chemical name | wt % |
|---|---|
| glycerin | 1.0 |
| tetrasodium EDTA | 0.1 |
| cetyl alcohol | 1.0 |
| stearyl alcohol | 1.0 |
| mineral oil | 5.0 |
| dimethicone | 1.0 |
| cyclomethicone | 0.5 |
| dimethiconol | 0.2 |
| polyquaternium-37 | 2.0 |
| steareth-21 | 1.0 |
| steareth-2 | 0.5 |
| salicylic acid | 2.0 |
| turmeric extract | 0.5 |
| triethanolamine to pH | 3.0 |
| water DI | qs to 100% |

EXAMPLE 8

The following oil-in-water emulsion within the scope of the invention is prepared:

| chemical name | wt % |
|---|---|
| xanthan gum | 0.2 |
| disodium EDTA | 0.1 |
| sodium PCA | 0.5 |
| diazodinyl urea | 0.3 |
| titanium dioxide | 1.0 |
| stearic acid | 3.0 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6.0 |
| turmeric extract | 0.5 |
| glycolic acid | 3.0 |
| malic acid | 2.0 |
| lactic acid | 2.0 |
| green tea extract | 1.0 |
| triethanolamine | to pH 3.8 |
| water DI | qs to 100% |

EXAMPLE 9

The following oil-in-water emulsion within the scope of the invention is prepared:

| chemical name | wt % |
|---|---|
| all-trans retinoic acid | 0.05 |
| light mineral oil | 10.0 |
| stearoxytrimethylsilane and stearyl alcohol | 5.0 |
| dimethicone | 2.0 |
| stearyl stearae | 10.0 |
| quaternium-15 | 3.0 |
| peg-22 dodecyl glycol copolymer | 1.0 |
| turmeric extract | 0.1 |
| sorbitol | 0.5 |
| methyl paraben | 0.2 |
| disodium EDTA | 0.1 |
| butylated hydroxytoluene | 0.1 |
| water DI | qs to 100% |

EXAMPLE 10

The following oil-in-water emulsion within the scope of the invention is prepared:

| chemical name | wt % |
|---|---|
| squalane | 20.0 |
| macadamia oil | 5.0 |
| pentaerythritol tetraoctanoate | 15.0 |
| petrolatum | 5.0 |
| glyceryl stearate | 3.0 |
| tocopherol acetate | 0.5 |
| butylated hydroxytoluene | 0.05 |
| methyl paraben | 0.15 |
| propyl paraben | 0.15 |
| retinol | 0.1 |
| turmeric extract | 0.25 |
| sodium citrate | 1.0 |
| ascorbic acid | 1.0 |
| butylene glycol | 2.0 |
| glycerol | 2.0 |
| bentone clay | 0.2 |
| disodium EDTA | 0.05 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin care composition having reduced irritation and sting, comprising:

(i) a cosmetic benefit ingredient selected from the group consisting of a hydroxy acid, retinol, retinoic acid, retinal, $C_2$–$C_5$ retinyl ester and mixtures thereof;

(ii) turmeric extract in an amount of from about 0.01 to about 20 wt. %; and (iii) a cosmetically acceptable vehicle.

2. The composition of claim 1 wherein the cosmetic benefit ingredient is a hydroxy acid, which is present in an amount of from about 0.01 to about 20% by weight of the composition.

3. The composition of claim 2 wherein the amount of the hydroxy acid is from about 0.1 to about 12% by weight of the composition.

4. The composition of claim 1 wherein the cosmetic benefit ingredient is a retinol or a retinyl ester, which is present in an amount of from about 33 to about 330,000 IU per gram of the composition.

5. The composition of claim 1 wherein the cosmetic benefit ingredient is selected from the group consisting of retinol, glycolic acid, lactic acid, and mixtures thereof.

6. A cosmetic method for reducing sting or irritation induced by the topical application of a composition containing a hydroxyacid or a retinoid, the method comprising topically applying turmeric extract.

* * * * *